(12) United States Patent
Burns et al.

(10) Patent No.: US 8,384,033 B2
(45) Date of Patent: Feb. 26, 2013

(54) QUANTIFICATION OF AN ABSORBER THROUGH A SCATTERING MEDIUM

(75) Inventors: David H. Burns, Pointe Claire (CA); Fabiano Pandozzi, Laval (CA)

(73) Assignee: The Royal Institute for the Advancement of Learning/McGill University, Montreal, Quebec (CA)

( * ) Notice: Subject to any disclaimer, the term of this patent is extended or adjusted under 35 U.S.C. 154(b) by 113 days.

(21) Appl. No.: 12/739,951

(22) PCT Filed: Nov. 10, 2008

(86) PCT No.: PCT/CA2008/001988
§ 371 (c)(1),
(2), (4) Date: Apr. 26, 2010

(87) PCT Pub. No.: WO2009/059433
PCT Pub. Date: May 14, 2009

(65) Prior Publication Data
US 2010/0249664 A1    Sep. 30, 2010

Related U.S. Application Data

(60) Provisional application No. 60/986,678, filed on Nov. 9, 2007.

(51) Int. Cl.
*G01J 5/02* (2006.01)

(52) U.S. Cl. .................................................. 250/341.8

(58) Field of Classification Search .... 250/338.1–338.5, 250/339.01–339.15, 340, 341.1–341.8, 342–353, 250/459.1
See application file for complete search history.

(56) References Cited

U.S. PATENT DOCUMENTS

| | | | |
|---|---|---|---|
| 5,706,821 A * | 1/1998 | Matcher et al. | 600/310 |
| 6,586,193 B2 | 7/2003 | Yguerabide et al. | |
| 6,630,673 B2 | 10/2003 | Khalil et al. | |
| 2002/0190213 A1* | 12/2002 | Bynum et al. | 250/341.8 |
| 2003/0030896 A1* | 2/2003 | Brooker | 359/368 |
| 2003/0064025 A1 | 4/2003 | Yang et al. | |
| 2003/0096302 A1 | 5/2003 | Yguerabide et al. | |
| 2005/0003517 A1* | 1/2005 | Ragless | 435/287.1 |
| 2009/0024360 A1* | 1/2009 | Arnvidarson | 702/189 |

* cited by examiner

*Primary Examiner* — Kiho Kim
(74) *Attorney, Agent, or Firm* — Merchant & Gould P.C.

(57) ABSTRACT

There is described a method for determining a quantitative parameter of a compound in an analysis sample, comprising: providing a scattering medium in physical contact with the analysis sample, the scattering medium having at least one layer, an index of refraction of the scattering medium being superior to an index of refraction of the analysis sample; propagating, in the scattering medium, an incident beam of light having a wavelength substantially corresponding to an absorption wavelength of the compound such that an evanescent wave is generated at an interface between the scattering medium and the analysis sample; taking n intensity measurements of a reflected beam of light for the analysis sample, n being superior to one; and determining the quantitative parameter of the compound using the n intensity measurements for the analysis sample.

19 Claims, 9 Drawing Sheets

QUANTIFICATION OF AN ABSORBER THROUGH A SCATTERING MEDIUM

RELATED APPLICATIONS

This application claims priority to U.S. Provisional application No. 60/986,678 filed Nov. 9, 2007, the entire contents of which are hereby incorporated by reference.

TECHNICAL FIELD

The present invention relates to the field of quantifying a compound in a sample, and particularly to the field of determination of an analyte concentration or concentration change in a sample.

BACKGROUND OF THE INVENTION

Analyte quantification is an important process in a range of diverse industries. Measurements made on a daily basis in a variety of areas such as pharmaceutical, medical and waste treatment are crucial for maintaining product quality and the well-being of communities. One common method for quantifying an analyte consists in extracting a portion of the analyte and measuring the analyte concentration. However, obtaining a sample for measurement is sometimes difficult. For example, for in vivo measurement of protein in cerebrospinal fluid (CSF) a lumbar puncture (spinal tap) is conducted to obtain a fluid sample. This procedure is not without risk, and as a result is not ideal.

Another method for determining the concentration of an analyte is the absorption measurement, which consists in measuring light after transmission through a sample. However, this method can be complicated by factors such as concentration range and light scattering. The latter process occurs when the direction of light is deviated due to irregular surfaces and/or index of refraction changes within samples. The scattering coefficient μs for a medium represents the average number of scattering events that a photon experiences per unit length of distance traveled. Similarly, the absorption coefficient μa represents the number of absorption events that occur per unit length of distance traveled. Diffuse light scattering complicates measurements since the path length of light is no longer a constant. This leads to an attenuation value that is not directly proportional to analyte absorption. Therefore this method is not suitable for the analysis of liquid samples contained in opaque plastic containers, such as medicine or Nalgene™ bottles. In this situation, the shape and scattering nature of the plastic would make a transmission measurement through the sample difficult.

Therefore there is a need for an improved method of quantification of a component or analyte in a sample which is fast and cost effective.

SUMMARY OF THE INVENTION

The present method and apparatus use an evanescent wave effect for determining the concentration of an analyte in a sample or an analyte concentration variation from one sample to another. An evanescent wave is a nearfield standing wave exhibiting exponential decay with distance and is generated at an interface between two mediums having different refractive indexes during a total internal refraction. The method and apparatus can also be used for determining the width of the medium having the highest refractive index.

The method and apparatus can be used for non-invasive sensing of a quantitative parameter. For example, glucose, lactate, pyruvate, or protein concentration in cerebrospinal fluid (CSF) or concentration variation in those analytes or compounds in CSF can be determined in a non-invasive manner, the skull of a patient corresponding to a scattering medium and the CSF of the patient corresponding to the sample comprising the analyte or compound.

In one embodiment, there is provided a method for determining a quantitative parameter of a compound in an analysis sample, comprising: providing a scattering medium in physical contact with the analysis sample, the scattering medium having at least one layer, an index of refraction of the scattering medium being superior to an index of refraction of the analysis sample; propagating, in the scattering medium, an incident beam of light having a wavelength substantially corresponding to an absorption wavelength of the compound such that an evanescent wave is generated at an interface between the scattering medium and the analysis sample; taking n intensity measurements of a reflected beam of light for the analysis sample, n being superior to one; and determining the quantitative parameter of the compound using the n intensity measurements for the analysis sample.

In accordance with a second broad aspect, there is provided a method for determining a property related to one of an analysis sample comprising a compound and a scattering medium, comprising: positioning the scattering medium in physical contact with the analysis sample, an index of refraction of the scattering medium being superior to an index of refraction of the analysis sample, the scattering medium having at least one scattering layer; propagating in the scattering medium an incident beam of light having a wavelength substantially corresponding to an absorption wavelength of the compound such that an evanescent wave is generated at an interface between the scattering medium and the analysis sample; taking n intensity measurements of a reflected beam of light for the analysis sample, n being superior to one; and determining the property of the compound using the n intensity measurements of the reflected beam of light for the analysis sample.

In accordance with a third broad aspect, there is provided a method for determining a thickness of a scattering medium, comprising: for each one of at least two samples comprising a compound and having an index of refraction inferior to an index of refraction of the scattering medium; positioning a sample in physical contact with the scattering medium; propagating in the scattering medium an incident beam of light having a wavelength corresponding to an absorption wavelength of the compound such that an evanescent wave is generated at an interface between the scattering medium and the sample; and taking n intensity measurements of a reflected beam of light for the sample, n being superior to one; and determining the thickness using a multivariate curve resolution method, non-negativity constraints, and the n intensity measurements for the at least two samples.

In accordance with a fourth broad aspect, there is provided a system for determining a quantitative parameter of a compound in an analysis sample, comprising: a processor in a machine, the processor being adapted to receive n intensity measurements of a reflected beam of light for the analysis sample, n being superior to one, the reflected beam of light resulting from a propagation of an incident beam of light in a scattering medium being in physical contact with the analysis sample such that an evanescent wave is generated at an interface between the scattering medium and the analysis sample, an index of refraction of the scattering medium being superior to an index of refraction of the analysis sample, the scattering medium having at least one scattering layer; and an application coupled to the processor, the application being configured for determining the quantitative parameter of the compound using the n intensity measurements of the reflected beam of light for the analysis sample.

In accordance with another broad aspect, there is provided a system for determining a thickness of a scattering medium, comprising: a processor in a machine, the processor being adapted to receive n intensity measurements of a reflected beam of light for at least two samples each comprising a compound, n being superior to one; and an application coupled to the processor, the application being configured for determining the thickness using a multivariate curve resolution method, non-negativity constraints, and the n intensity measurements for the at least two samples, for each one of the at least two samples, the reflected beam of light resulting from a propagation of an incident beam of light in the scattering medium being in physical contact with the sample such that an evanescent wave be generated at an interface between the scattering medium and the sample, an index of refraction of the scattering medium being superior to an index of refraction of the sample.

In accordance with a further broad aspect, there is provided a system for determining a property related to one of an analysis sample comprising a compound and a scattering medium, the system comprising: a first support for receiving the analysis sample; a second support for receiving the scattering medium having an index of refraction superior to an index of refraction of the analysis sample, the scattering medium having at least one scattering layer, the first support and the second support being positioned such that the scattering medium and the analysis sample be in physical contact; a light source adapted to emit an incident beam of light having a wavelength corresponding to an absorption wavelength of the compound; at least one photodetector adapted to take n intensity measurements of a reflected beam light for the analysis sample, the reflected beam of light resulting from a propagation of the incident in the scattering medium such that an evanescent wave be generated at an interface between the scattering medium and the analysis sample; and a property determining module connected to the at least one photodetector and adapted to determine the property in accordance with the n intensity measurements of the reflected beam of light for the analysis sample.

An analyte or compound should be understood as a chemical or biological element of a sample. The sample can be a liquid, a solid or a gas. The compound can be any constituent part of the sample. In an embodiment, the analyte or compound is a biomarker.

A scattering medium is a medium having an index of refraction superior to the index of refraction of the sample. The scattering medium can be a solid, a liquid, or a gas.

The term "quantitative parameter" of a compound is used to define either the concentration of the compound in the sample or the concentration variation of the compound. When the term "quantitative parameter" refers to the concentration variation, this variation can be the concentration variation of a compound in a single sample over time or the concentration variation of a compound from one sample to another sample, each comprising the compound.

In accordance with a further aspect, there is provided a method or system as described herein wherein the compound is a biomarker and the analysis sample is a fluid in the subject, e.g. a human. In one aspect the biomarker may be lactate, pyruvate, glucose, or protein, e.g. haemoglobin or a cytochrome c enzyme, In another aspect, the fluid is cerebrospinal fluid (CSF). In yet another aspect, the fluid is amniotic fluid, ocular fluid, or blood.

In accordance with yet a further aspect, there is provided a method for measuring a biomarker in a subject, e.g. the concentration or concentration variation of a biomarker in a subject. Also provided herein is a method for diagnosis or prognosis of a medical condition in a subject comprising using the methods or systems described herein to measure a compound (e.g. a biomarker) in a subject, wherein the concentration of the compound or a change in the concentration of the compound in the subject is prognostic or diagnostic of a medical condition.

In accordance with another aspect, there is provided a method for monitoring efficacy of a therapeutic treatment or for monitoring disease progression in a subject comprising using the methods or systems described herein to measure a compound (e.g. a biomarker) in a subject, wherein the concentration of the compound or a change in the concentration of the compound indicates efficacy of the therapeutic treatment or progression of the disease.

BRIEF DESCRIPTION OF THE DRAWINGS

Having thus generally described the nature of the invention, reference will now be made to the accompanying drawings, showing by way of illustration, an embodiment or embodiments thereof, and in which.

DETAILED DESCRIPTION

We describe the use of evanescent wave effects for the estimation of an absorbing layer held behind a scattering layer. In general, a larger source/detector separation in a reflectance measurement will lead to photons arriving at the detector that have spent a longer time within the scattering medium. This allows us to relate a time-dependent photon time-of-flight experiment to the proposed steady state experiment. Furthermore, measurements allow the estimation of analyte concentration for samples where scattering is relatively high and for a range of scattering layer thicknesses. The methods described herein provide a simplified way in which to probe samples that are typically inaccessible to optical measures.

Figure 1:
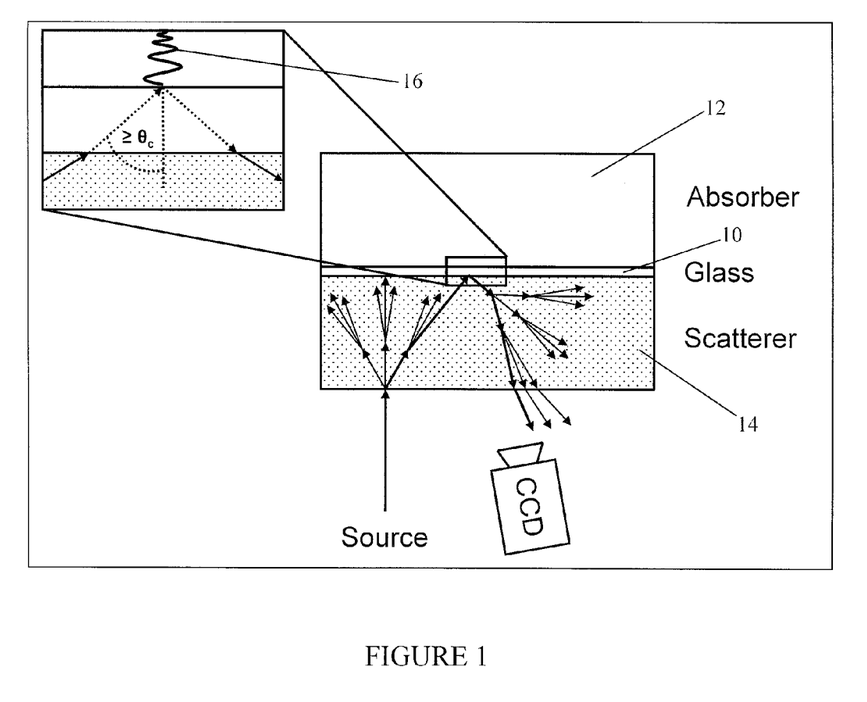
FIG. 1 illustrates the generation of an evanescent wave at the interface between a glass layer and an absorbent layer, in accordance with an embodiment.

During total internal reflection of light at an interface between two mediums having different refraction indices, an evanescent wave is generated substantially at the interface, on the side of the medium having the lowest refraction index. The depth of penetration of the evanescent wave in the lowest refraction index medium is usually less than the wavelength of the light. FIG. 1 illustrates the generation of an evanescent wave at the interface between a glass layer 10 and an absorbent sample 12. The glass layer 10 is sandwiched between the absorbent sample 12 and a scattering layer 14. The glass layer 10 and the scattering layer 14 both have an index of refraction superior to that of the sample layer 12 and the index of refraction of the glass layer 10 is superior to that of the scattering layer 14. For example, the index of refraction can be equal to "1.4" for the scattering layer 14, to "1.5" for the glass layer 10, and "1.33" for the absorbent layer 12. Light is injected in the scattering layer 14 and this incident light is propagating through the scattering layer 14. While it is propagating in the scattering layer 14, light is scattered. Part of light then propagates in the glass layer 10 since the refraction index of the glass layer 10 is superior to that of the scattering layer 14. When light rays reaches the interface between the glass layer 10 and the absorbent layer 14 with an angle superior to the critical angle θc, total internal reflection occurs and an evanescent wave 16 is generated. The critical angle θc is defined as follows:

$$\theta c = \sin^{-1}(n_{absorbent\ layer}/n_{glass})$$ (Eq. 1)

This intensity of the evanescent wave 16 is dependent on the light wavelength, the indices of refraction of the different layers 10, 12, 16, and the optical configuration. The evanescent wave 16 is then reflected in the glass layer 10 and propagates in the glass layer 10 and the scattering layer 14 while experiencing scattering. This results in a reflected ray of light which exits from the scattering layer 14.

While FIG. 1 illustrates the generation of an evanescent wave 16 in a system comprising three layers, it should be understood that the glass layer 10 can be omitted or additional layers may added.

Figure 2:
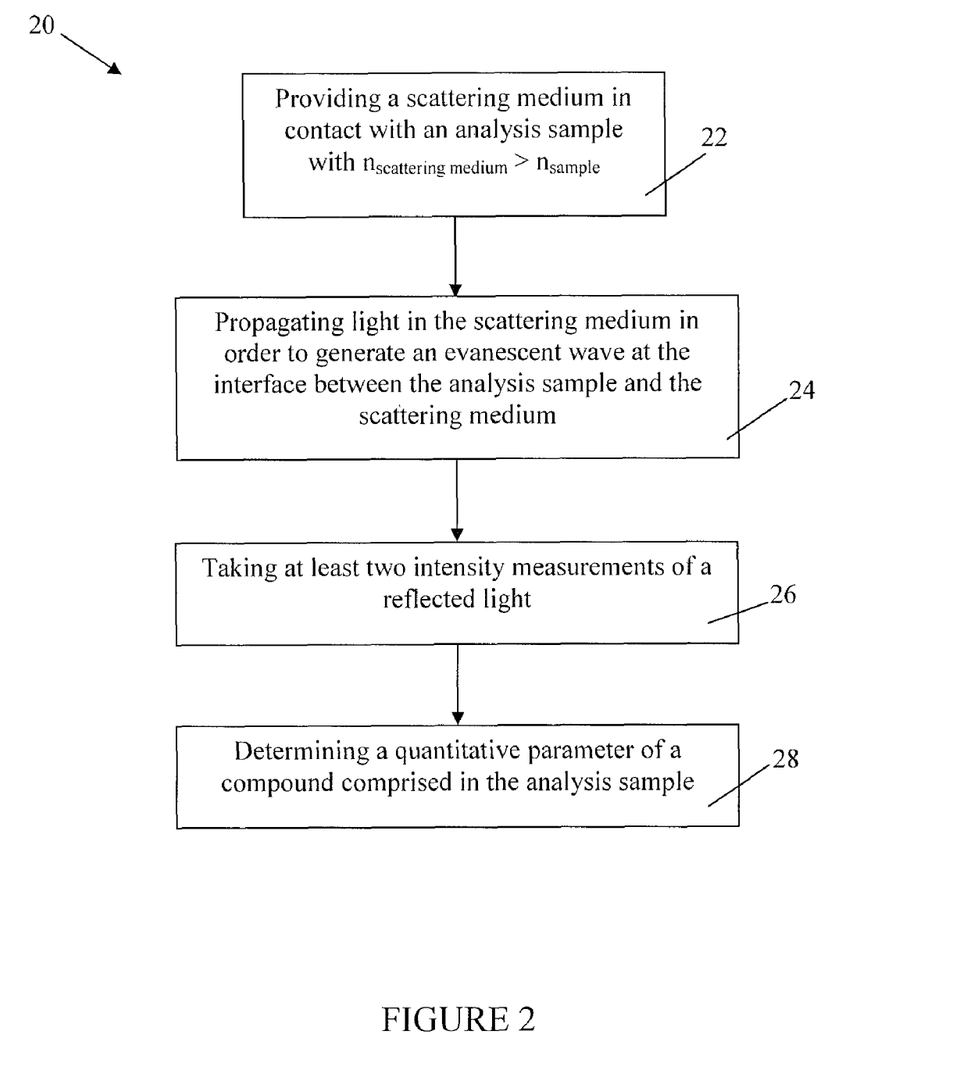
FIG. 2 is a flow chart of a method for determining a quantitative parameter of a compound in a sample, in accordance with an embodiment.

FIG. 2 illustrates one embodiment of a method 20 for determining a quantitative parameter of a compound in an analysis sample. The first step 22 of the method consists in providing a scattering medium in physical contact with the analysis sample. When the scattering medium and the analysis sample are in physical contact, no air is present between them, for example. The scattering medium comprises at least one scattering layer. The index of refraction of the different scattering layers are chosen such that a total internal refraction of an incident beam of light occurs at the interface between the analysis sample and the scattering layer of the scattering medium in contact with the analysis sample.

In one embodiment, a solid scattering medium is provided. If the sample is a solid, the scattering medium and the sample are positioned so that they are in physical contact. If the sample is a liquid or a gas, the scattering medium can be the container used to receive the sample.

In another embodiment, the scattering medium comprises two scattering layers. For example, a glass layer can be provided between the highly scattering layer and the sample, as illustrated in FIG. 1.

The second step 24 is the propagation of an incident beam of light in the scattering medium in order to generate an evanescent wave at the interface between the scattering medium and the analysis sample. The light has a wavelength which substantially corresponds to an absorption wavelength of the compound of which the quantitative parameter is to be determined. Any light source having the corresponding wavelength can be used to generate the incident beam of light. The incident beam of light propagates through the scattering medium and at least a portion of the incident beam experiences a total internal reflection at the interface which is accompanied with the generation of the evanescent wave, as illustrated in FIG. 1. The evanescent wave is then reflected and exits from the scattering medium.

The third step 26 of the method 20 is the measurement of at least two intensities of the reflected beam of light which exits from the scattering medium. In other words, n intensity measurements are taken, n being superior to one. Any method and apparatus for measuring a light intensity can be used. For example, the intensities can be measured using a Charge-Coupled Device (CCD) camera.

In one embodiment, the measurement of the n intensities comprises the measurement of the intensity of the reflected beam of light at n different distances from the light source position.

In another embodiment, the measurement of the n intensities comprises the measurement of the intensity of the reflected beam of light at n different instants of time from a single distance from the light source position.

The last step 28 of the method 20 is the determination of the quantitative parameter of the compound. The quantitative parameter can be either a concentration or a concentration variation. The quantitative parameter can be determined from the n measured intensities since a relation exists between the measured intensities and the absorption of the evanescent wave by the compound which occurs in the sample.

In one embodiment, a stagewise multi-linear regression (SMLR) technique is used to calculate the quantitative parameter of the compound. The general multi-linear equation relating the concentration C ($1 \times p$) to the measured intensities $I_1, \ldots, I_n$ of the reflected light is given by:

$$C = b_0 + b_1 x_1 + \ldots + b_n x_n$$ (Eq. 2)

Where $x_1, \ldots, x_n$ correspond to $\log(I_1), \ldots, \log(I_n)$, respectively, $b_1, \ldots, b_n$ are weighting coefficients, p is the number of estimated properties, and n is the number of intensity measurements.

When the quantitative parameter corresponds to a concentration, it is possible to determine the concentration C of the compound in the sample, by knowing the weighting parameters and measuring the n reflected intensities.

In one embodiment of the method 20, the weighting parameters are determined by measuring n intensities of the reflected beam of light for at least three reference samples in which the compound is present in different concentrations. For example, if the lactate concentration in CSF is determined using the method illustrated in FIG. 2, the reference samples can be CSF samples taken from different patients or taken from a single patient at different times. Knowing the concentration and the reflected intensities for each one of the reference samples, the weighting parameters are determined using equation 2.

When the quantitative parameter corresponds to a concentration variation, only (n−1) weighting coefficients $b_1, \ldots, b_n$ are needed to determine the concentration variation. For example, if two intensity measurements are performed for the analysis sample and a reference sample, the concentration variation between the analysis sample and the reference sample can be determined using the two weighting coefficients $b_1$ and $b_2$. In this case the method 20 further comprises the steps of providing the reference sample comprising the compound in a reference concentration, positioning the scattering medium in physical contact with the reference sample, injecting the light in the scattering medium and measuring at least two intensities for the reflected light. Then the concentration variation between the analysis sample and the reference sample can be determined by applying equation 2 to the analysis sample and to the reference sample to obtain their respective concentration formula. The concentration variation is obtained by subtracting the concentration formula. If the reference concentration of the reference sample is known, then it is possible to determine the concentration of the compound in the analysis sample.

In one embodiment, the number of intensity measurements is chosen to better relate changes in the measured data to the quantitative parameter. Models using different numbers of measured intensities can be generated and tested using independent data sets. Selection of the most parsimonious model can be accomplished using an f-test at a 95% confidence interval. Details of the SMLR model selection are provided in "Applied Regression Analysis", Draper, N. and H. Smith, Second ed. 1981, New York: Wiley. An error of a specific model is tested against another model to determine whether there is a significant difference at a specified confidence level. If there is no significant difference, the model with fewer parameters is selected as the most parsimonious. Otherwise, the model with a larger number of parameters is chosen. Effectiveness of each model can be tested by calculating the coefficient of variance (CV) and $r^2$ values.

Figure 3A:
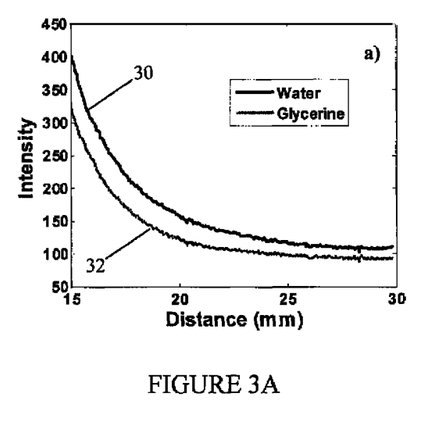
FIG. 3A is a graph of the intensity of a reflected light as a function of a distance between a light emitter and a photodetector for a water sample and a glycerine sample, in accordance with an embodiment.

FIG. 3A illustrates the measured reflected intensity as a function of the distance between the light source and the detector used to measure the reflected intensity for a water sample 30 and a glycerine sample 32. The experimental set-up is the one illustrated in FIG. 1. The glycerine sample is a mixture of water and glycerine in particular proportions. The reflected light intensity is lower for the glycerine sample (curve 32) than for the water sample (curve 30). Since the index of refraction of glycerine is equal to 1.47, a mixture of water and glycerine has an index of refraction superior to that of water. As a result, the probability of generating evanescent waves is inferior for a glycerine sample than for the water sample, which leads to less back scattered light by the glycerine sample than by the water sample. Therefore increasing the proportion of glycerine in the glycerine sample results in the decrease of the intensity of the reflected light. For a certain glycerine proportion in the glycerine sample corresponding to an index of refraction of 1.4 for the glycerine sample, total internal reflection is no longer possible since light travels in the forward direction through the glycerine sample. This corresponds to a glycerine content of 52%, at which point attenuation becomes negligible as glycerine proportion is further increased.

Figure 3B:
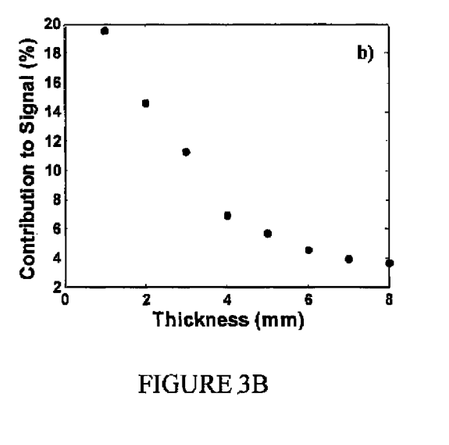
FIG. 3B is a graph of the contribution of evanescence to the detected signal as a function of the scattering thickness layer for a glycerine sample, in accordance with an embodiment.
Figure 4A:
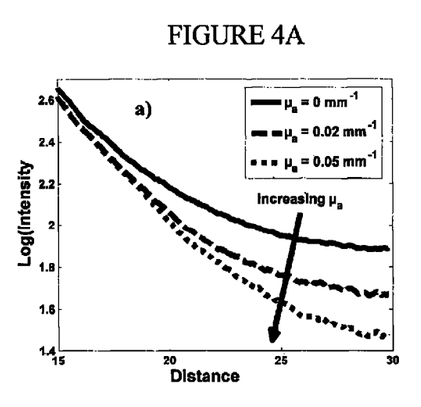
FIGS. 4A-4D are graphs of the intensity of a reflected light for various samples having an increasing absorption coefficient $\mu_a$ as a function of the distance between a light emitter and a photodetector for a scattering thickness layer of 1 mm (A), 3 mm (B), 5 mm (C), and 8 mm (D), in accordance with an embodiment.
Figure 4B:
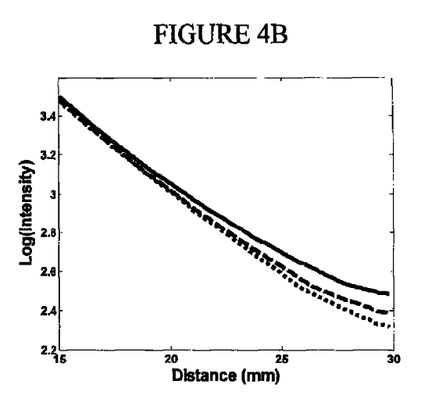
Figure 4C:
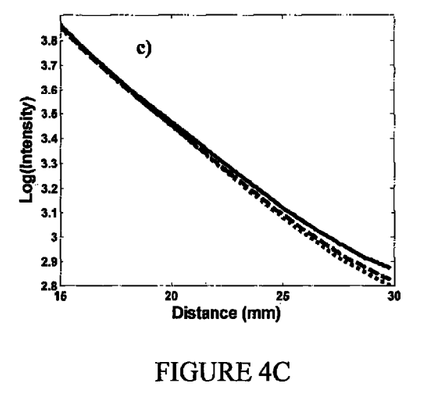
Figure 4D:
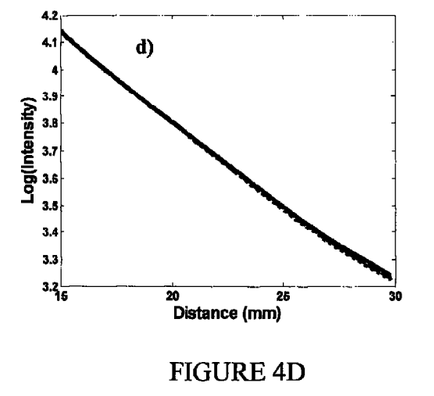

FIG. 3B illustrates the relative contribution of evanescence to the measured reflected light as a function of the thickness of the scattering medium. The experimental set-up is as illustrated in FIG. 1. The relative contribution of evanescence is determined by calculating the area ratio between the intensity profile of the glycerine sample and the intensity profile of the water sample. From FIG. 3B, one can see that a thinner scattering layer increases the relative contribution of evanescence and therefore improves the estimation of the quantitative parameter of the compound. For example, the relative contribution from evanescence with an 8 mm scattering layer is only about one fifth of that with a 1 mm scattering layer.

FIGS. 4A-4D illustrate the intensity of the reflected light as a function of the distance between the light source and the light detector for samples having different absorption coefficients as the thickness increases from FIG. 4A to FIG. 4D. In each one of FIGS. 4A to 4D, increasing the coefficient of absorption results in a decrease of the intensity of the reflected light. However, as thickness is increased from FIG. 4A to FIG. 4D, one can see that the magnitude of the reflected intensity decrease is reduced since larger thicknesses correspond to longer path lengths which in turn reduce the intensity originating from the evanescent wave. From FIGS. 4A to 4D, one can see that the reflected intensity decrease from a sample to another increases with the distance between the light source and the light detector. As a result, the most promising region of interest appears to be further away from the light source using this optical configuration. If a single point detector is used, this multi element detector method is useful in pinpointing where the detector should be placed for optimal information recovery.

Table 1 presents results from the SMLR analysis for the estimation of absorption coefficients. Table 1 shows the SMLR results calibration of concentration estimations at each individual thickness. The $r^2$ regression coefficients and coefficient of variations (CV) are given for a set of calibration data and an independent test set. The specific positions used in the regression are presented in the BP column.

TABLE 1

Results from SMLR analysis for the estimation of absorption coefficients

| Thickness (mm) | Cal | | Test | | BP |
| --- | --- | --- | --- | --- | --- |
| | $R^2$ | CV (%) | $R^2$ | CV (%) | |
| 1 | 0.99 | 7.2 | 0.98 | 12.4 | 210, 116 |
| 2 | 0.99 | 6.9 | 0.97 | 13.8 | 206, 156 |
| 3 | 0.98 | 11.8 | 0.96 | 16.1 | 235, 1 |
| 4 | 0.97 | 13.6 | 0.93 | 23.2 | 222, 200 |
| 5 | 0.96 | 16.6 | 0.94 | 20.7 | 250, 10 |
| 6 | 0.96 | 16.8 | 0.94 | 20.4 | 244, 184 |
| 7 | 0.96 | 16.2 | 0.96 | 18.4 | 241, 201 |
| 8 | 0.93 | 21.5 | 0.93 | 21.6 | 250, 192 |

Referring back to FIG. 2, the determination of the quantitative parameter 28 in one embodiment of the method 20 is performed according to a Multivariate Curve Resolution (MCR) approach, also known as Self Modeling Curve Resolution. The use of an MCR method allows the estimation of the underlying physical processes, such the scattering process and the absorption process, resulting in the obtained measured reflected intensities. A person skilled in the art should understand that MCR methods are known in the art. For example, one can refer to "Self modeling curve resolution", Lawton, W. H. and E. A. Sylvestre, 1971. 13(3): p. 617-633, to "Excitation-emission-lifetime analysis of multicomponent systems—I. Principal component factor analysis", Russell, M. D. and M. Gouterman, Spectrochimica Acta, Part A, 1988. 44(9): p. 857-861, or to "Triplet sublevel emission of platinum tetrabenzoporphyrin by spectrothermal principal component decomposition", Aartsma, T. J., et al., Porphyrins. Journal of American Chemical Society, 1982. 104: p. 6278-6283, to better understand the MCR approach.

The MCR model of the measured data decomposes the signal into corresponding loadings and scores, as illustrated in the following equation [14]:

$$D = CS^T + E \quad \text{(Eq. 3)}$$

where D (I×J) is the matrix of the measured intensities with I rows and J columns with I being the number of spectral profile and J being the length of each of these profiles. C (I×N) represents the profile of each individual component present in the signal, each component corresponding to an underlying process, with N being the number of components, and S (J×N) represents the unit response profiles for each of these components. S (J×N) may be defined as a score or as the amount of each component present in the sample. E (I×J) is the residual error between the actual data and the C and S matrices.

When the MCR model is used, the method 20 further comprises the steps of providing at least one reference sample comprising the compound, and for each one the reference sample, positioning the scattering medium in physical contact with the reference sample, injecting the light in the scattering medium and measuring at least two intensities for the reflected light. The matrix D presents the measured intensities for the analysis sample and the reference samples. The first step of the resolution of Equation 3 is the determination of the principal components using an eigenvector decomposition of the matrix D. Using non-negativity constraints and rotation, the component vectors are obtained. The variance represented by each component is calculated from the singular value matrix obtained during the decomposition just mentioned. The quantitative parameter of the compound in the analysis sample is then determined as described below.

In one embodiment, two principal components are sufficient in representing a majority of the variance in the data. One component is related to the thickness of the scattering medium and the other component is related to the evanescent wave.

Figure 5A:
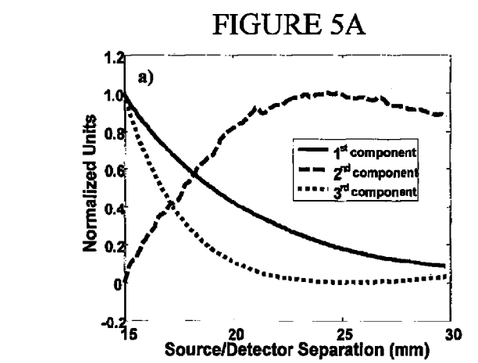
FIG. 5A is a graph of the normalized value of three components after rotation as a function of the distance between a light emitter and a photodetector, in accordance with an embodiment.
Figure 5B:
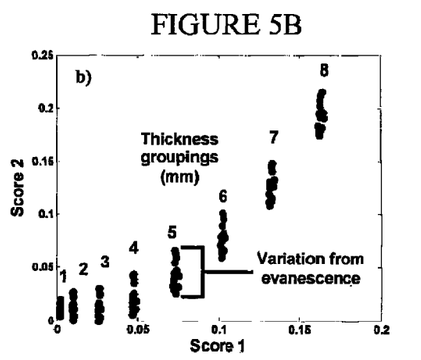
FIG. 5B is a graph of the score of a second component related to the evanescent wave as a function of the score of a first component related the thickness of a scattering medium, in accordance with an embodiment.

In another embodiment, the data is composed of three principal components, which are able to express more than 99.9% of the variance in the data. The non-negative contributions are obtained by making a rotation of these component vectors. The rotated components for the example illustrated in FIG. 1 are illustrated in FIG. 5a. In this case, two independent sets of samples, namely an analysis sample and a reference sample, are used. The absorption changed over eight different concentrations in each set of samples. For each concentration, eight different thicknesses of the scattering medium are used. The first and third components of the signal are monotonically decreasing profiles that are well fit by single exponential decay curves ($r2 > 0.99$). The second component, on the other hand, has a non-monotonic profile with a peak maximum. While the first component is related to the thickness of the scattering medium, the second component is related to the evanescent wave. This peak maximum is near a source/detector separation of 24 mm, and the profile has a lightly sloping decay afterwards. The contribution to the signal from each component is given by their respective scores. Each contribution arises from a different underlying process, which can be best illustrated by looking at score correlation plots. FIG. 5B illustrates the relationship between the scores from the first component and the second component for the different samples measured. For each of the different scattering layer thicknesses, the first component presents a tight grouping of points (labeled 1 through 8). The second component has a variation with changes in absorption level for each sample. As a result, the variation of concentration of the compound between the analysis sample and any one of the reference samples can be determined from FIG. 5B, since the variation concentration is related to the variation in the score of the second component. If the concentration of a reference sample is known, then the concentration of the compound in the analysis sample is determined in accordance with the concentration variation determined from FIG. 5B.

Figure 5C:
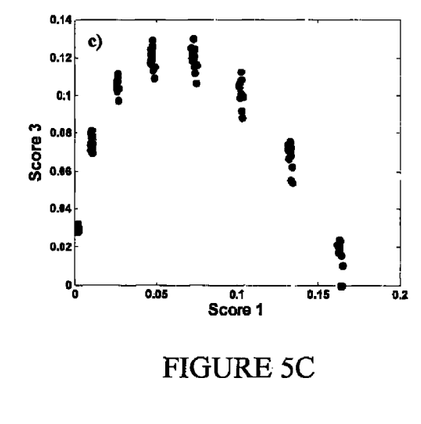
FIG. 5C is a graph of the score of a third component as a function of the score of a first component related the thickness of a scattering medium, in accordance with an embodiment.

The origin of the third component is thought to be from a second minor scattering component. FIG. 5C illustrates the relationship between the third and first component scores. There is a shift from low values of the third scores at small scattering medium thicknesses, followed by an increase as the thickness is increased. Once a thickness of 4-5 mm is achieved, a maximum appears to be reached, followed by a decrease in values. These results show that the third contribution is from a reflection since the light source has a certain divergence angle as it enters the sample. When the thickness of scattering medium is modified, the angles of light that can be seen by the detector are changed. Based on this experimental configuration, thicknesses of 4 to 5 mm appear to be the maximum range.

Figure 5D:
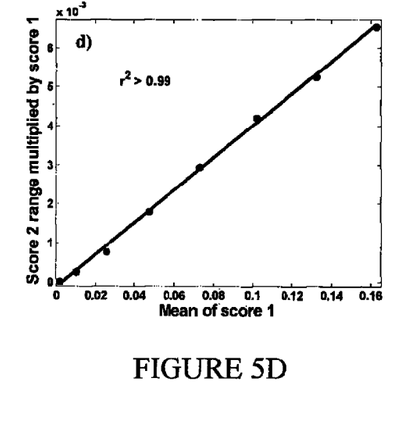
FIG. 5D is a graph of the range of a second component score multiplied by a first component score as a function of the first component score when normalized to the first component score.

FIG. 5D illustrates the relationship between the range of the second component scores multiplied by the first component scores as a function of the first component scores when normalized to the first component scores. This relationship is well fit by a simple linear equation ($r^2 > 0.99$). In one embodiment, for large ranges of scattering medium thickness, only extreme values may be needed for calibration while still allowing for accurate absorption measurements.

In one embodiment, for both methods used for determining the quantitative parameter, the region of highest correlation at all thicknesses is typically further away from the light source. As thickness is increased, the most highly correlated region moves further away from the source. For example, when all possible data points are used for the model building, at 1 mm scattering medium thickness, the highest correlated region is 27.5 mm whereas at 8 mm thickness it is 29.8 mm, because light diffusion affects the total internal reflection events.

Figure 6:
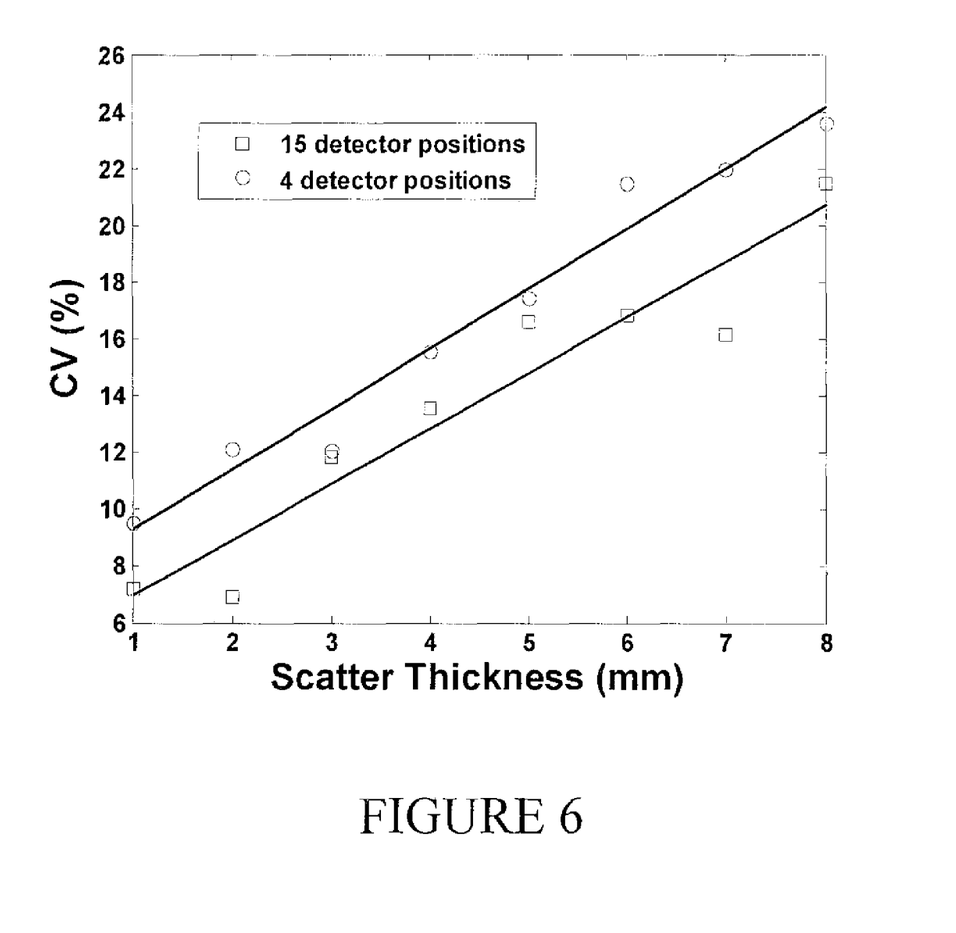
FIG. 6 is a graph of an error associated with a quantitative parameter as a function of the thickness of a scattering layer, in accordance with an embodiment.

FIG. 6 illustrates the error of the two-point calibration models generated using the two quantitative parameter resolution approaches described above. The squares represent the CV for models using 15 unique detector positions, each selected based on highest correlation to compound concentration. The circles represent the CV of models built based on a subset of only 4 best detector positions. Both methods show a clear increase in error about the models when the scattering medium thickness is increased. The estimation effectiveness is lowered as thickness is increased. This is a direct consequence of the photon pathlength being increased significantly through the scattering media, which leads to a decrease in backscattered information at a given detector position. Evanescent field information then becomes more difficult to recover from the background intensity. It should be noted that in general, the error when using only 4 unique detector positions is only marginally higher than when using all 15 positions. According to FIG. 6, the quantitative parameter can be determined with two detector positions when the scattering layer thickness is about 2 to 5 mm.

It should be understood that any wavelength corresponding to an absorption wavelength of the compound can be used. For example visible wavelength can be used for determining the quantitative parameter. In an embodiment, the observed signal is optimized using near-infrared (NIR) wavelengths because less scattering is present for longer wavelengths. For tissue measurements, the scattering level may be reduced by approximately three times when NIR wavelengths are used in comparison to visible wavelengths. FIG. 6 shows that errors below 15% can be expected for tissue samples having thicknesses about to 1 cm. The method 20 can therefore be used for non-invasive probing using NIR wavelengths.

While the present description refers to the use of a single wavelength for determining the quantitative parameter of a compound in a sample, it should be understood that more than one wavelength can be used. For example, two different wavelengths, each corresponding to an absorption wavelength of the compound, can be used to calculate either the concentration or the concentration variation of the compound.

While the present description refers to the MCR and SMLR techniques to determine the quantitative parameter of a compound in a sample in accordance with the measured intensities, it should be understood that any technique known by a person skilled in the art can be used.

It should be understood that in one embodiment the methods 20 and 40 may be integrated in a single method for determining a property related to one of an analysis sample comprising a compound and a scattering medium. In this embodiment the single method comprises the steps of positioning the scattering medium in physical contact with the analysis sample, an index of refraction of the scattering medium being superior to an index of refraction of the analysis sample; propagating in the scattering medium an incident beam of light having a wavelength substantially corresponding to an absorption wavelength of the compound so that an evanescent wave is generated at an interface between the scattering medium and the analysis sample; taking n measurements of the intensity of a reflected beam of light for the analysis sample, n being superior to one; and determining the property of the compound using the n intensity measurements of the reflected light for the analysis sample.

In one embodiment, the property is the concentration of the compound in the analysis sample or the concentration variation between the analysis sample and at least one reference sample. In this case, the step of calculating the property is performed in accordance with the step 28 of the method 20.

In another embodiment, the property is the thickness of the scattering medium and the step of calculating the property is performed in accordance with the steps 42 to 48 of the method 40.

Figure 7:
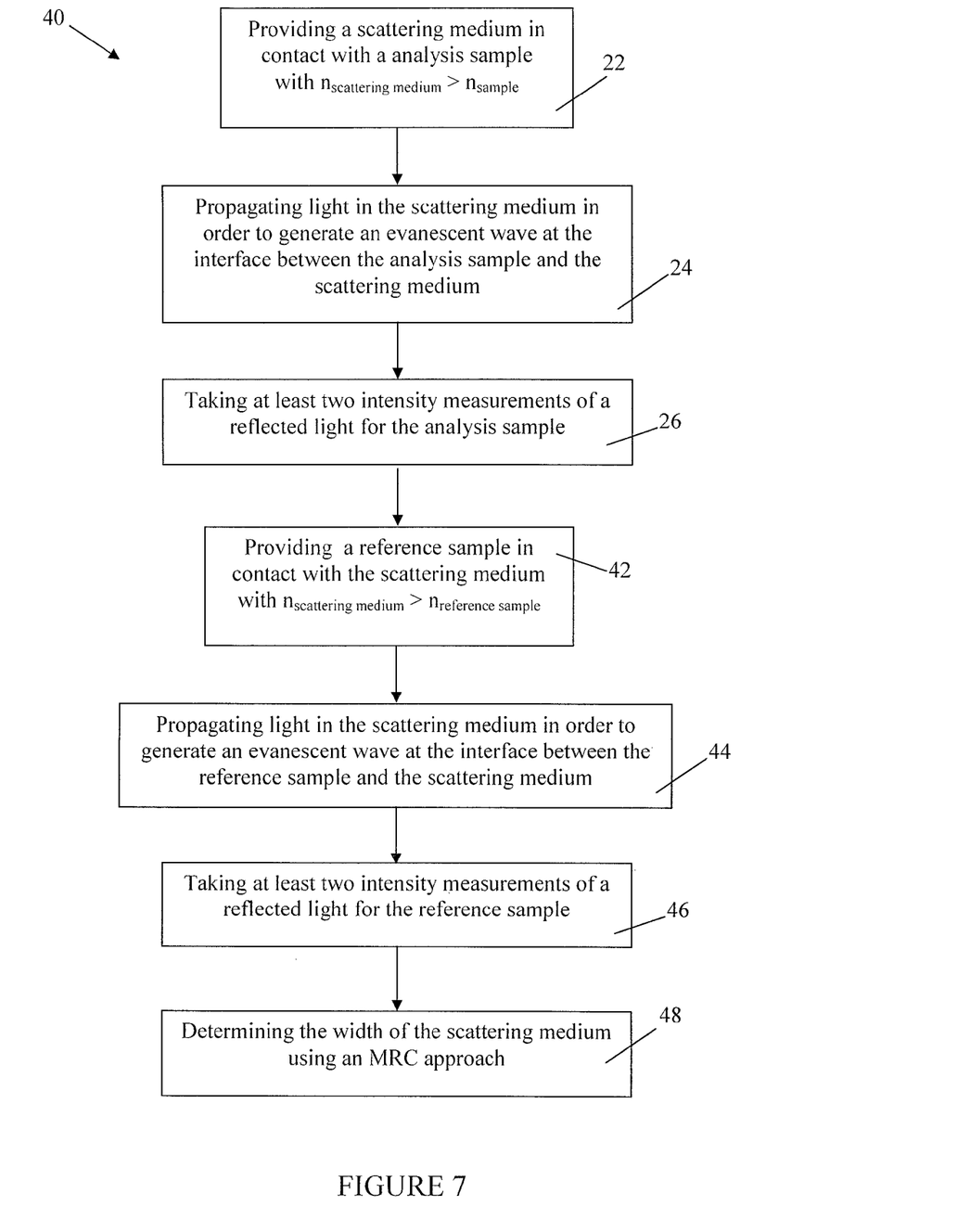
FIG. 7 is a flow chart of a method for determining the thickness of a scattering layer, in accordance with an embodiment.

FIG. 7 illustrates one embodiment of a method 40 for determining the thickness of a scattering medium. The first three steps of the method 40 corresponds to the steps 22, 24, and 26 of the method 20. The fourth step 42 of the method 40 consists in providing a reference sample in physical contact with the scattering medium. The index of refraction of the reference sample is lower than that of the scattering medium. The fifth step 44 is the injection of light using the same light source as in step 24 into the scattering layer. Light propagates while scattering until it reaches the interface between the scattering layer and the reference sample. An evanescent wave is generated at the interface and gives rise to a reflected light. The sixth step 46 of the method consists in measuring at least two intensities of the reflected light. The last step of the method is the determination of the thickness of the scattering medium using the MCR approach. By plotting the score of the component related to the absorption as a function of the score of the component related to the scattering, the thickness of the scattering layer is determined as being the x-coordinate of the points, as illustrated in FIG. 5B. The thickness of the scattering medium is given by the score of the first component.

In one embodiment, the MCR resolution comprises a third component. In this case, the thickness can also be determined by plotting the score of the third component as a function of the score of the component related to the scattering. The thickness of the scattering layer is determined as being the x-coordinate of the points, as illustrated in FIG. 5C.

In one embodiment, a system for determining a quantitative parameter of a compound in a sample comprises a processor in a machine and an application coupled to the processor. The processor is adapted to receive the value of the measured intensities and the application is adapted to determine the quantitative parameter in accordance with the methods described above.

In one embodiment, a system for determining the thickness of a scattering medium comprises a processor in a machine and an application coupled to the processor. The processor is adapted to receive the value of the measured intensities and the application is adapted to determine the thickness in accordance with the methods described above.

Figure 8:
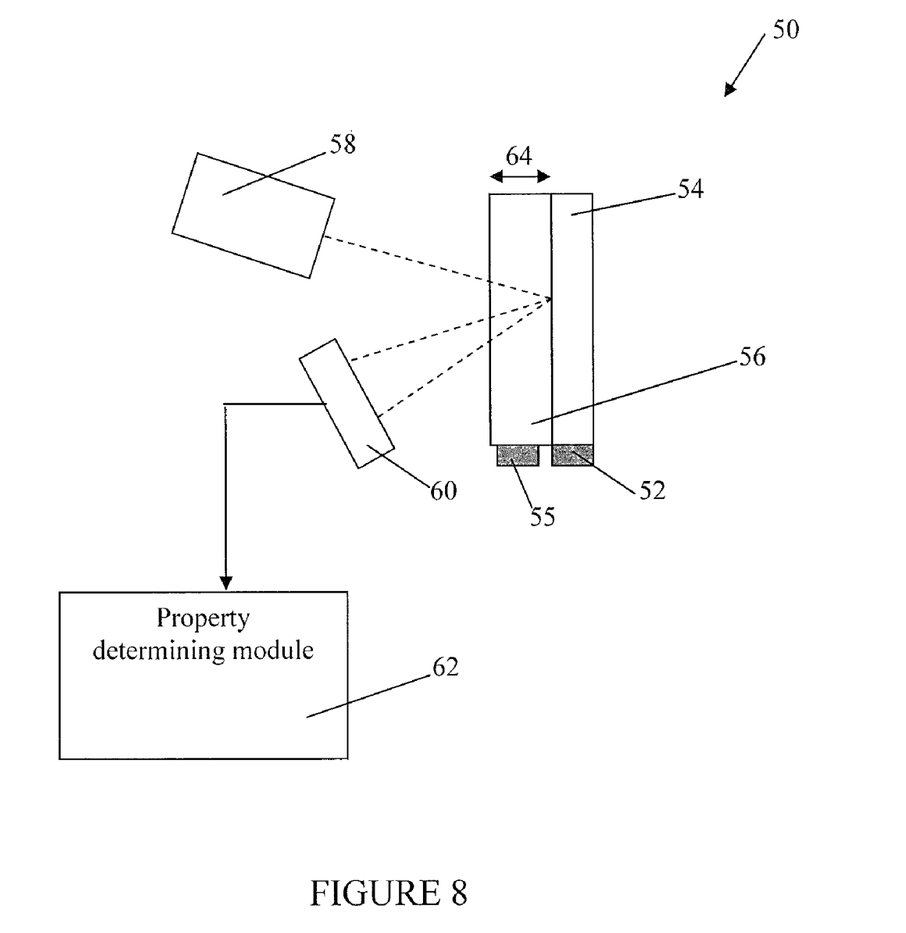
FIG. 8 is a block diagram of a system for determining a property related to one of a quantitative parameter of a compound in a sample and a thickness of a scattering medium, in accordance with an embodiment.

FIG. 8 illustrates one embodiment of a system 50 for determining a property related to a device comprising a analysis sample and at least one scattering medium. The system comprises a support 52 for receiving a sample 54, a support 55 for receiving at least one scattering medium 56, a light emitter 58, a photodetector 60, and a property determining module 62.

The support 52 can be adapted to receive a solid, a liquid or a gas sample. For example, the support can be a cell adapted to receive a liquid. If the sensing light propagates through the support 52 before reaching the analysis sample 54, the support 52 is made of any material which allows the generation of an evanescent wave at the surface of the sample 54. Alternatively, the support 52 can comprise a window made of any appropriate material and the sensing light propagates through the window in order to reach the sample 54.

The scattering medium 56 is positioned in physical contact with the sample 54. The scattering medium 56 can be a liquid surrounding the sample 54. in the support 52. In another example, the support 52 can be a tank having two compartments, a first one for receiving the sample 54 and a second one for receiving the scattering medium 56. The separation between both compartments is made of a material adapted to allow the generation of an evanescent wave at the surface of the sample 54.

The light emitter 58 generates a light beam which is directed towards the scattering medium 56. The light has a wavelength corresponding to an absorption wavelength of the compound present in the sample. Light propagates in the scattering medium 56 while scattering. An evanescent wave is generated substantially at the surface of the sample 54 and a reflected light is generated.

It should be understood that any light source emitting an adequate wavelength can be used. For example, lasers or LEDs can be used to generate the light beam.

The photodetector 60 measures the intensity of the reflected light at at least two different distances from the light emitted 58. It should be understood that the photodetector can measure any optical quantity related to the intensity and this optical quantity can be subsequently converted into a corresponding intensity. Any photodetector adapted to detect the wavelength emitted by the light emitter 58 can be used. For example, the photodetector 60 can be a CCD camera.

In one embodiment, the system 50 comprises at least two photodetectors positioned at different distances from the light emitter 58. Each photodetector measures a corresponding intensity of the reflected light. In another embodiment, a single photodetector is used to measure the intensity of the reflected light at least two instants in time. It should be understood that any number of photodetectors or combination of photodetectors adapted to measure at least two intensities of the reflected light can be used.

The photodetector 60 is connected to the property determining module 62 which is adapted to receive the measured intensities from the photodetector 60 and to determine an experimental factor. In the case, the photodetector 60 measures an optical quantity different from the intensity. The property determining module 62 is further adapted to determine the intensities corresponding to the measured optical quantities.

In one embodiment, the property determining module 62 is adapted to determine a quantitative parameter in accordance with the method 20 illustrated above.

In another embodiment, the property determining module 62 is adapted to determine the thickness or width 64 of the scattering medium 56 in accordance with the method 40 illustrated above.

In one embodiment, the distance between the light emitter 58 and the light detector 60 is chosen so that to improve the signal-to-noise ratio and to have an improve correlation with the quantitative parameter of the compound.

Figure 9:
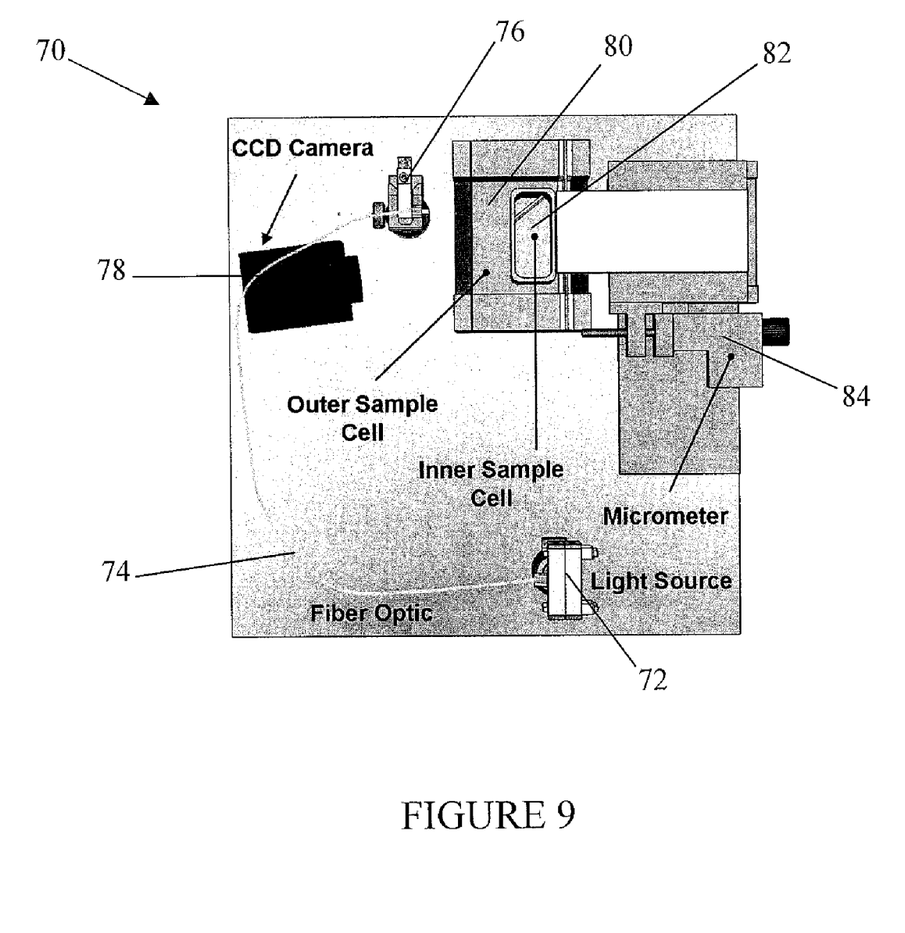
FIG. 9 illustrates a system comprising an optical fiber for determining a property related to one of a quantitative parameter of a compound in a sample and a thickness of a scattering medium, in accordance with an embodiment.

FIG. 9 illustrates an embodiment of a system 70 in which the thickness of the scattering medium is variable. The system 70 comprises a light source 72, an optical fiber 74, a fiber connector 76, a CCD camera 78, an outer cell 80 for receiving the scattering medium, an inner cell 82 for receiving a sample, and a micrometer 84.

The light source 72 is connected to the optical fiber 74 which is positioned in front of the outer cell 80. The optical fiber 74 is maintained in position by the fiber connector 76. The injection angle of the light beam outputted by the optical fiber 74 may have any value. In one embodiment, the light beam emitted by the optical fiber 74 is substantially perpendicular to the surface of the outer cell 80.

The outer cell 80 is adapted to receive a liquid scattering medium and the inner cell 82. The outer cell 80 is made of any material allowing the light to cross the outer cell 80 and propagates into the scattering medium. The inner cell 80 is movable with respect to the outer cell 80 and is made of any material allowing the generation of an evanescent wave at the surface of the sample comprised in the inner cell 82. The inner cell is connected to a micrometer 84 such that the position of the inner cell 84 within the outer cell 80 can be changed. As a result, the thickness of the scattering medium comprised between the sample and the optical fiber 74 can be changed.

The CCD camera 78 measures at least two intensities of the reflected light and is connected to the property determining module 62 (not shown in FIG. 9).

The present methods and systems can be used for determining the concentration or variation of concentration of a compound in a sample when the sample is contained in an opaque plastic container. They can also be used for in vivo measurement of a concentration or concentration variation of a compound or analyte, e.g. a biomarker.

It is contemplated that the present invention can be carried out as a method, can be embodied in a system, a computer readable medium or an electrical or electro-magnetic signal.

The methods and systems described herein have application in a variety of areas where quantification through optically turbid layers would be valuable. For example, the methods may be used for analysis of samples through opaque containers, in vivo measurements and in-line monitoring of reactions. There is a great need in medicine, for example, to measure biological markers in a sample or in a subject in vivo, without the need for invasive procedures which can be risky, expensive or time-consuming. For example, analysis of amniotic fluid can yield valuable diagnostic and prognostic information, but often requires that a fluid sample be obtained by amniocentesis. Analysis of cerebrospinal fluid (CSF) is also of great medical value and again often requires an invasive procedure to obtain a sample from the patient. There is also a need to analyze liquid samples contained in opaque plastic containers, such as medicine or Nalgene™ bottles.

The methods and systems provided herein can be used to monitor reactions or to monitor the components of reservoirs in, for example, industrial fermentation methods, large-scale chemical syntheses, or other commercial processes. It is contemplated that the methods presented herein can be applied to any area where the ability to analyse the concentration of components, such as analytes, compounds, and biological markers, in an absorbing layer hidden behind a highly scattering layer, is desirable. In the methods provided herein, the experimental setup is not complex and can be adapted to a wide range of areas for the analysis of a multitude of samples. Some of these include in vivo analyses of fluid within the skull, amniotic fluid or ocular fluids as well as samples contained in opaque plastic containers and reservoirs.

The terms "patient", "subject", "mother", "fetus", "offspring" and other similar terms relating to subjects and their body parts are intended herein to relate to humans and non-humans, unless otherwise explicitly indicated. In one aspect, the subject is a human.

The term "biological marker" (also referred to herein as "biomarker") includes one or more biochemical indices such as glucose, lactate, pyruvate or another metabolic acid or metabolite; proteins such as insulin, insulin like growth factors (IGFs) and their binding proteins, haemoglobin, cytochrome enzymes; and/or fatty acids. A biological marker may comprise any molecule, such as a protein or a metabolite, which is found in a biological sample and can be measured using the methods described herein.

In one embodiment, the methods and systems described herein are used to measure biomarkers, e.g. to measure concentration or concentration variation of a biomarker, in a fluid in a subject, e.g. a human. For example, lactate production has been promoted as a major detrimental factor in ischemic brain damage and elevated lactate may be an early marker of brain injury in inflicted traumatic brain injury. In an embodiment, there is provided herein a method for measuring biomarkers in the brain, such as lactate. Non-limiting examples of other biomarkers which may be measured in the brain include haemoglobin and cytochrome enzymes. Haemoglobin, only present in red blood cells, provides an indicator of blood oxygenation, and the cytochrome enzymes in the oxidative metabolic pathway provide an indicator of tissue oxygenation. The methods and systems described herein can be used to monitor, continuously and non-invasively, haemodynamic and metabolic variables in human organs, such as the brain. These measurements are useful for prognosis and diagnosis of a wide range of conditions, such as brain injury, stroke, autonomic failure and sleep disorders in adult patients, as well as for characterization of neurophysiological processes in the adult and developing infant brain. In an embodiment, compounds, e.g. biomarkers, are measured in the brain of a subject through the skull, i.e. without the need for invasive procedures.

It is known in the art that biological tissues (e.g. human tissues) contain a variety of substances whose absorption spectra at NIR wavelengths are well defined. Some absorbing compounds, such as oxygenated haemoglobin (HbO2), deoxyhaemoglobin (Hb), and oxidised cytochrome oxidase (CtOx), have concentrations in tissue which are strongly linked to tissue oxygenation and metabolism. Other effective absorbers include melanin, found in the epidermis layer of skin; other haemoglobin compounds such as carboxyhaemoglobin, (HbCO), which may be present in significant quantities in the tissue in some subjects, haemiglobin (Hi) and sulfhaemoglobin (SHb), which may become significantly raised in some diseases of the liver or in malaria; and myoglobin.

CtOx is the terminal enzyme in the cellular respiratory chain, and is located in the mitochondrial membrane. The enzyme contains four redox active groups; two haem iron (a and a3) and two copper (CuA and CuB) centers. These four metal centers change their redox state (i.e. accept or donate electrons) during electron turnover of the enzyme. The oxygen binding site of the enzyme is the binuclear unit which is formed of the CuB and haem a3. It is the donation of electrons from this unit to oxygen which accounts for the great majority of oxygen consumption in biological tissue. In an embodiment, the methods and systems described herein are used to measure change in redox state of CtOx, i.e. oxidized vs. reduced forms of the enzyme. The change in redox state of CtOx may be used, for example, as an indicator of oxygen availability at a cellular level and ultimately of cell metabolism.

In the brain, there are many chromophores of interest, including for example HbO2, Hb and CtOx, whose concentrations vary with oxygenation. Quantified changes in the concentration of Hb and HbO2 using the methods described herein can be used to measure absolute haemodynamic parameters such as cerebral blood flow and cerebral blood volume.

In another embodiment, the methods and systems described herein are used to measure compounds, e.g. biomarkers, in the cerebrospinal fluid (CSF). Non-limiting examples include detection and measurement in CSF of the level of IgG production by the central nervous system, which has been applied to the diagnosis of multiple sclerosis; detection and measurement in CSF of the level of nerve growth factor (NGF), cholinesterases AChE and BChE, tau, phospho-tau, -amyloid, and apo E, which have been associated with Alzheimer's disease; markers of inflammation; metabolites such as lactate; and so on. Biomarkers in the CSF have been used to predict severity of injury and long-term outcome, to identify patients early who are at risk, and to evaluate effectiveness of therapeutic interventions. It is contemplated that the methods described herein can be used to measure levels of compounds, e.g. biological markers, which correlate with one or more medical conditions. In one aspect, the methods and systems described herein are used to measure lactate, pyruvate, glucose or protein, e.g. haemoglobin or a cytochrome c enzyme, in the CSF of a subject.

In one embodiment, the invention provides a method of analyzing amniotic fluid in situ in a subject, e.g. without disrupting the amniotic sac, for example without insertion of any instrument into the amniotic sac. For example, a method is provided for measuring one or more selected biological markers in amniotic fluid in situ. In one aspect, the methods described herein may be used for analyzing amniotic fluid in situ in a pregnant subject having an amniotic sac containing amniotic fluid. One or more selected biological markers in amniotic fluid can be measured. Such measurement of biological markers can be useful for diagnosis and prognosis, for example to predict risk of developing a medical condition in the mother and/or the fetus, to predict birth weight of the fetus, and/or for diagnosis or prognosis of medical conditions. For example, the methods described herein can be used to measure insulin or glucose concentration in the amniotic fluid which would be of use in the diagnosis of fetal hyperinsulinism, neonatal hypoglycaemia, and/or gestational diabetes mellitus (GDM). It is contemplated that the methods described herein may be applied to any animal having an amniotic fluid sac.

In another embodiment, there is provided herein a method for measuring biomarkers in the blood, for example blood metabolites such as lactate, pyruvate and glucose. For example, in critical care, the continuous monitoring of blood lactate is of significant importance. Lactate can be used as a marker for the assessment of tissue perfusion and oxidative capacity and abnormal levels of lactate in the blood may occur in individuals suffering myocardial infarction, cardiac arrest, circulatory failure, emergency trauma and the like. Measurements of lactate levels are therefore of prognostic and diagnostic significance.

In yet another embodiment, the methods and systems described herein are used to measure bladder volume or urine volume or changes in bladder or urine volume in a subject. Urinary bladder dysfunction afflicts millions of people worldwide. This condition not only leads to loss of voluntary control over the bladder muscles, but also cuts off sensorial feedback to the central nervous system, which leaves patients incapable of sensing bladder fullness and gauging the right moment to trigger bladder voiding. Measurements of bladder volume or of urine volume are critical to restore voluntary control of the bladder, by alerting the patient to the appropriate time to micturate. Methods such as catheterization have been used for bladder volume assessment, but such methods are highly invasive and have the risk of infecting the bladder.

The contents of all documents and references cited herein are hereby incorporated by reference in their entirety.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for determining a quantitative parameter of a biological marker in a fluid of a subject in vivo, the fluid being in physical contact with a biological scattering medium having at least one layer, an index of refraction of said scattering medium being superior to an index of refraction of said fluid;
propagating, in said scattering medium, an incident beam of light having a wavelength substantially corresponding to an absorption wavelength of said biological marker such that an evanescent wave is generated at an interface between said scattering medium and said fluid;
taking n intensity measurements of a reflected beam of light for said fluid, n being superior to one; and
determining said quantitative parameter of said biological marker using said n intensity measurements for said fluid.

2. A method as claimed in claim 1, wherein said taking n intensity measurements comprises measuring an intensity of said reflected beam of light for said fluid at n different distances from an emitter of said incident beam of light.

3. A method as claimed in claim 1, wherein said taking n intensity measurements comprises measuring an intensity of said reflected beam of light for said fluid at n different instants in time.

4. A method as claimed in claim 1, wherein said determining said quantitative parameter comprises determining said quantitative parameter using a stagewise multi-linear regression.

5. A method as claimed in claim 4, wherein said determining said quantitative parameter comprises determining a concentration of said biological marker in said fluid using n weighting parameters.

6. A method as claimed in claim 1, wherein said determining said quantitative parameter comprises determining said quantitative parameter using a multivariate curve resolution method and non-negativity constraints.

7. A method for diagnosis or prognosis of a medical condition or for monitoring efficacy of a therapeutic treatment or for monitoring disease progression in a subject comprising using the method of claim 1 to measure a biological marker in the subject, wherein the concentration of the biological marker or a change in the concentration of the biological marker in the subject is prognostic or diagnostic of a medical condition or indicates efficacy of the therapeutic treatment or progression of the disease.

8. The method of claim 1, wherein bladder volume, urine volume or a change in bladder or urine volume are measured in the subject.

9. The method according to claim 1, wherein said biomarker is protein, lactate, pyruvate or glucose; said protein is haemoglobin or a cytochrome c enzyme; said fluid is cerebrospinal fluid or amniotic fluid; and said subject is a human.

10. The method according to claim 1, wherein the fluid is cerebrospinal fluid and the biological scattering medium comprises a skull of the subject.

11. A method for determining a thickness of a scattering medium, comprising:
for each one of at least two samples comprising a compound and having an index of refraction inferior to an index of refraction of said scattering medium,
positioning a sample in physical contact with said scattering medium;
propagating in said scattering medium an incident beam of light having a wavelength corresponding to an absorption wavelength of said compound such that an evanescent wave is generated at an interface between said scattering medium and said sample; and
taking n intensity measurements of a reflected beam of light for said sample, n being superior to one; and
determining said thickness using a multivariate curve resolution method, non-negativity constraints, and said n intensity measurements for said at least two samples.

12. A system for determining a quantitative parameter of a biological marker in an fluid of a subject in vivo, comprising:
a processor in a machine, said processor being adapted to receive n intensity measurements of a reflected beam of light for said fluid, n being superior to one, said reflected beam of light resulting from a propagation of an incident beam of light in a biological scattering medium being in physical contact with said fluid such that an evanescent wave is generated at an interface between said scattering medium and said fluid, an index of refraction of said scattering medium being superior to an index of refraction of said fluid, said scattering medium having at least one scattering layer; and
an application coupled to said processor, said application being configured for determining said quantitative parameter of said biological marker using said n intensity measurements of said reflected beam of light for said fluid.

13. A system as claimed in claim 12, wherein said processor is adapted to receive said n intensity measurements of said reflected beam of light for said fluid taken at n different distances from an emitter of said incident beam of light.

14. A system as claimed in claim 12, wherein said processor is adapted to receive said n intensity measurements of said reflected beam of light for said fluid taken at n different instants in time.

15. A system as claimed in claim 12, wherein said application is further configured for said determining said quantitative parameter using a stagewise multi-linear regression.

16. A system as claimed in claim 15, wherein said application is further configured for determining said quantitative parameter to be a concentration of said biological marker in said fluid using n weighting parameters.

17. A system as claimed in claim 12, wherein said application is further configured for determining said quantitative parameter using a multivariate curve resolution method and non-negativity constraints.

18. A system for determining a thickness of a scattering medium, comprising:
a processor in a machine, said processor being adapted to receive n intensity measurements of a reflected beam of light for at least two samples each comprising a compound, n being superior to one; and
an application coupled to said processor, said application being configured for determining said thickness using a multivariate curve resolution method, non-negativity constraints, and said n intensity measurements for said at least two samples,
for each one of said at least two samples, said reflected beam of light resulting from a propagation of an incident beam of light in said scattering medium being in physical contact with said sample such that an evanescent wave be generated at an interface between said scattering medium and said sample, an index of refraction of said scattering medium being superior to an index of refraction of said sample.

19. A system for determining a property related to one of a fluid of a subject in vivo and a biological scattering medium, the fluid comprising a biological marker and being in physical contact with the scattering medium, the scattering medium having at least one layer, an index of refraction of said scattering medium being superior to an index of refraction of said fluid, said system comprising:
a light source adapted to emit an incident beam of light having a wavelength corresponding to an absorption wavelength of said biological marker;
at least one photodetector adapted to take n intensity measurements of a reflected beam light for said fluid, said reflected beam of light resulting from a propagation of said incident in said scattering medium such that an evanescent wave be generated at an interface between said scattering medium and said fluid; and
a property determining module connected to said at least one photodetector and adapted to determine said property in accordance with said n intensity measurements of said reflected beam of light for said fluid.

* * * * *